US009884153B2

(12) United States Patent
Holmqvist et al.

(10) Patent No.: US 9,884,153 B2
(45) Date of Patent: *Feb. 6, 2018

(54) MEDICAMENT DELIVERY DEVICE

(71) Applicant: Carebay Europe Ltd., Swatar (MT)

(72) Inventors: Anders Holmqvist, Varmdo (SE);
Stefan Loof, Skondal (SE)

(73) Assignee: Carebay Europe Ltd., Swatar (MT)

( * ) Notice: Subject to any disclaimer, the term of this patent is extended or adjusted under 35 U.S.C. 154(b) by 38 days.

This patent is subject to a terminal disclaimer.

(21) Appl. No.: 14/963,647

(22) Filed: Dec. 9, 2015

(65) Prior Publication Data

US 2016/0101235 A1 Apr. 14, 2016

Related U.S. Application Data

(63) Continuation of application No. 14/394,993, filed as application No. PCT/EP2013/057390 on Apr. 9, 2013, now Pat. No. 9,302,059.

(30) Foreign Application Priority Data

Apr. 17, 2012 (SE) ...................................... 1250381

(51) Int. Cl.
*A61M 5/31* (2006.01)
*A61M 5/50* (2006.01)
*A61M 5/20* (2006.01)

(52) U.S. Cl.
CPC ................ *A61M 5/31* (2013.01); *A61M 5/20* (2013.01); *A61M 5/5086* (2013.01);
(Continued)

(58) Field of Classification Search
CPC ........ A61M 5/31; A61M 5/20; A61M 5/5086; A61M 2207/00; A61M 2005/3142;
(Continued)

(56) References Cited

U.S. PATENT DOCUMENTS 9,302,059 B2 * 4/2016 Holmqvist .......... A61M 5/5086

FOREIGN PATENT DOCUMENTS

WO 2011092518 A2 8/2011
WO 2011124632 A1 10/2011

* cited by examiner

*Primary Examiner* — Manuel Mendez
(74) *Attorney, Agent, or Firm* — McDonnell Boehnen; Hulbert & Berghoff LLP (57) ABSTRACT

A medicament delivery device has proximal and distal ends; a medicament container with a plunger, a neck portion, and a delivery member unit; a housing extending along a longitudinal axis with proximal and distal open ends; a drive unit configured to apply a force on the plunger; and a C-shaped tubular body with a longitudinal slit/gap such that body can be attached to the neck portion forming a container unit. The C-shaped body also has an inner support configured to interact with the neck portion and with the delivery member unit and prevent the medicament container from moving relative to the body after the medicament container is attached to the body, and outer support configured to interact with a corresponding support of the housing to prevent the C-shaped tubular body from moving relative to the housing after the container is arranged within the housing through the distal open end.

29 Claims, 10 Drawing Sheets

Related U.S. Application Data (60) Provisional application No. 61/625,409, filed on Apr. 17, 2012.

(52) U.S. Cl.
CPC ............... *A61M 2005/2006* (2013.01); *A61M 2005/3142* (2013.01); *A61M 2207/00* (2013.01)

(58) Field of Classification Search
CPC .. A61M 2005/2006; A61M 2005/2013; A61M 2005/202; A61M 2005/2026; A61M 5/315; A61M 5/31503; A61M 2005/31506; A61M 2005/31508; A61M 2005/3151; A61M 2005/3139
USPC ................. 604/110, 192, 197, 208, 220, 111
See application file for complete search history.

MEDICAMENT DELIVERY DEVICE

CROSS REFERENCE TO RELATED APPLICATIONS

The present application is a continuation application of U.S. patent application Ser. No. 14/394,993, filed Oct. 16, 2014, which is a 371 of International Patent Application No. PCT/EP2013/057390, filed Apr. 9, 2013 which claims the benefit of U.S. Provisional Patent Application No. 61/625,409, filed Apr. 17, 2012 which also claims the benefit of Swedish Patent Application No. 1250381-9, filed Apr. 17, 2012 the entire contents of which are incorporated entirely herein by reference.

TECHNICAL AREA

The present invention relates to a medicament delivery device for use in combination with a C-shaped tubular body capable of holding a medicament container within the medicament delivery device.

BACKGROUND OF INVENTION

Pre-filled medicament containers are used in a vast variety of medicament delivery devices and in particular for self-administration of medicament. Many of the medicament containers used are pre-filled containers that are placed in the medicament delivery devices before delivery. In order to make the medicament delivery device ready for delivery of medicament a medicament delivery member, such as an injection needle, is attached to a proximal end of the container.

In order to standardize the connection between the medicament container tip and the delivery member, e.g. an injection needle, the luer taper system has been developed. It comprises two variants, the luer slip and the luer lock systems. The luer taper system has been widely accepted and used due to its relative simplicity, which also facilitates handling and attachment of the delivery member to the medicament container.

However, a drawback with most medicament delivery systems has been that they can be opened and closed unnoticed, a shortcoming which favours tampering and even product counterfeits. There is thus a demand for devices that are easy to use but that still provide tamperproof connection of a delivery member with a medicament container.

In view of the above mentioned demand, a tamper evident luer lock closure unit or TELC unit, has been developed. It comprises an attachment part having a luer lock or luer taper fitting. To the attachment part a closure cap is threadedly connected and thus the closure cap is twisted off when removed—not lifted off.

The controlled twisting motion has the advantage that accidental spillage of the medication is largely avoided, which otherwise often occurs with other types of delivery member shields that are pulled off, because of the jerky opening action.

The tamper evident function comprises lugs on the closure cap that are released by the twisting motion, which lugs then immediately drop away slightly. It is practically impossible to close the syringe again completely, whereby it is evident that the closure cap has been removed.

Even though the TELC unit has a number of advantages, there are some issues that need to be addressed in conjunction with medicament delivery devices, and in particular devices having a certain degree of functionality such as for example auto-injection. Because the TELC unit has a rather large and in particular wide cap, with a diameter that is often larger than the diameter of the medicament container, it may be difficult to fit it into a container holder or housing, in particular if the medicament container is arranged with a circumferentially outwardly directed flange, often made integral with the medicament container. It is then impossible to position the medicament container in a tubular holder or housing unless it is inserted from the distal end of the holder or housing. Even so, the support in the proximal end of the medicament container may not be adequate since there is an annular gap between the outer surface of the proximal area of the medicament container and the holder or housing.

One solution to solve this problem is to attach the TELC unit to the proximal end of the medicament container after the medicament container has been placed in the holder or housing in order to have the medicament container with the TELC unit in the operative position within the medicament delivery device. This is not optimal since it would demand a more expensive process of assembling a medicament container with a TELC unit in a holder or a housing of a medicament delivery device. It would demand that the medicament container is placed in the holder or in the housing directly after filling the container with medicament, that the TELC unit is attached to the container and then that the assembled container with the TELC unit is sterilized. Further, if the container with the TELC unit is to be used in a reusable medicament delivery device, the container with the TELC unit must be provided to a patient or to a user. Then the container with the TELC unit must be delivered to the patient or to the user as a unit which is sterilized. The container and the TELC unit cannot be delivered in two parts to be assembled by the user.

BRIEF DESCRIPTION OF INVENTION

The aim of the present invention is to remedy the drawbacks as mentioned above.

The solution according to a one aspect of the invention relates to a medicament delivery device having a proximal and an opposing distal end. Said device comprises a medicament container comprising a movable plunger, a neck portion and a delivery member unit; a longitudinally extending housing (in the following referred to as the housing) along a longitudinal axis A and having a proximal open end and an opposing distal open end; a drive unit arranged at the distal end of the housing and configured to apply a force on the movable plunger; a C-shaped tubular body comprising a longitudinally extending slit/gap such that said C-shaped tubular body can be attached to the neck portion of said medicament container forming a container unit wherein said C-shaped tubular body further comprises: inner support means configured to interact with the neck portion and with the delivery member unit of said medicament container such that said medicament container is prevented from being moved in relation to the C-shaped tubular body, after the medicament container is attached to said C-shaped tubular body, and outer support means configured to interact with corresponding support means of the housing such that said C-shaped tubular body is prevented from being moved in relation to the housing after the container unit is arranged within said housing through the distal open end.

The delivery member unit comprises an attachment part and a closure cap/shield removably connected to the attachment part. The attachment part is fixedly connected to the medicament container. The delivery member unit may further comprise a delivery member, preferably an injection needle or the like which is surrounded by the shield. The delivery member unit is a TELC-unit in the embodiment described as below.

The inner support means comprises at least one longitudinally extending and radial inwardly directed ledge on the inner circumferential surface of the C-shaped tubular body configured to interact with at least one longitudinally extending indentation on the outer surface of the attachment part, such that said medicament container is prevented from being rotated in relation to the C-shaped tubular body.

The inner support means further comprises a continuous annular radial inwardly directed ledge or discrete annular radial inwardly directed ledges on the inner circumferential surface of the C-shaped tubular body configured to interact with the neck portion of said medicament container and with the distal annular surface of the attachment part, such that said medicament container is prevented from being longitudinally moved in relation to the C-shaped tubular body. Supporting the medicament container around its neck portion provides a good force-distributing contact surface.

The outer support means comprises a continuous annular surface or discrete annular surfaces on the outer circumferential surface of the C-shaped tubular body facing towards the proximal end of the device configured to interact with a corresponding continuous annular surface or discrete annular surfaces arranged on the inner circumferential surface of the housing facing towards the distal end of the device, such that said C-shaped tubular body is prevented from passing through the proximal open end of the housing after the container unit is arranged within said housing through the distal open end of the housing.

The outer support means further comprises first and second opposed lateral edges forming the longitudinally extending slit/gap, said lateral edges being configured to interact with longitudinally extending and radial inwardly directed ledges or ribs arranged on the inner circumferential surface of the housing, such that the container unit is prevented to be rotated in relation to the housing.

The medicament delivery device according to any one of the preceding features is an injection device, preferably and auto-injection device.

The C-shaped tubular body enables a secure support and hold of the medicament container around its neck portion whereby in combination with the outer support means, the medicament container will be prevented to be moved in relation to the housing such that any forces applied on the medicament container during medicament delivery will be taken up by the neck portion. Such forces may be considerable if an automatic injection function is used, wherein powerful compression springs are often employed for moving a plunger rod and a stopper inside the medicament container in the proximal direction.

In many instances, a housing of a medicament delivery device has a generally elongated tubular shape and particularly the part of the medicament delivery device arranged to accommodate the medicament container, since the latter often may have a tubular elongated shape. Therefore, said C-shaped tubular body may also have a generally tubular shape provided with a longitudinally extending slit/gap. The slit or gap may facilitate the mounting of the C-shaped tubular body on the medicament container, in particular since the holder device also may have a certain flexibility or elasticity, which may enable it to flex such that the slit may be enlarged so that the medicament container may pass. In this respect, the material of the holder device may be chosen so as to allow this flexibility and elastic deformation.

Because the C-shaped tubular body preferably is designed to cooperate with the neck portion of the medicament container, said inner support means comprises a continuous annular radial inwardly directed ledge or discrete/multiple annular radial inwardly directed ledges. These ledge(s) may be designed to be in contact with the surface of the neck portion to provide a firm support and seat for the medicament container. The ledge(s) may of course be designed in many ways that provide support surfaces for the neck portion of the medicament container. They may also include protrusions, interrupted surfaces or one or several annular surfaces. The surfaces may have shapes that are complementary to the shape of the neck portion of the medicament container.

According to one preferred use of the present invention, the delivery member unit of the medicament container is a TELC-unit fixedly connected/attached to the medicament container. In order to provide a positive connection between the C-shaped tubular body and the medicament container in this aspect, a proximal tubular portion of the holder device may have a configuration to house an attachment part of the TELC-unit.

In connection with the use of a TELC-unit, the inner and outer support means facilitate the removal of the closure cap/shield of the TELC-unit since the attachment part is held fixed to the C-shaped tubular body, and the C-shaped tubular body is held fixed to the housing, thereby replacing a grip from a user on the attachment part. The closure cap may therefore be removed by twisting it with one hand and holding the housing of medicament delivery device with the other hand.

Since the attachment part of a TELC unit is often arranged with grip members on its outer surface, said already existing grip members may be used to interact with the inner support means of the C-shaped tubular body. Indeed, many other shapes and designs may be used that may perform the gripping action of the attachment part.

It may further be advantageous to prevent rotation of the C-shaped tubular body in relation to the housing of the medicament delivery device, and in particular when a TELC-unit is utilised, requiring a twisting action. Therefore, said first and second opposed lateral edges forming the longitudinal slit may be configured to cooperate with longitudinally extending and radial inwardly directed ledges or ribs arranged on the inner circumferential surface of the housing, such that the container unit is prevented to be rotated in relation to the housing. The slit or gap will in this aspect have a dual function.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

Figure 1:
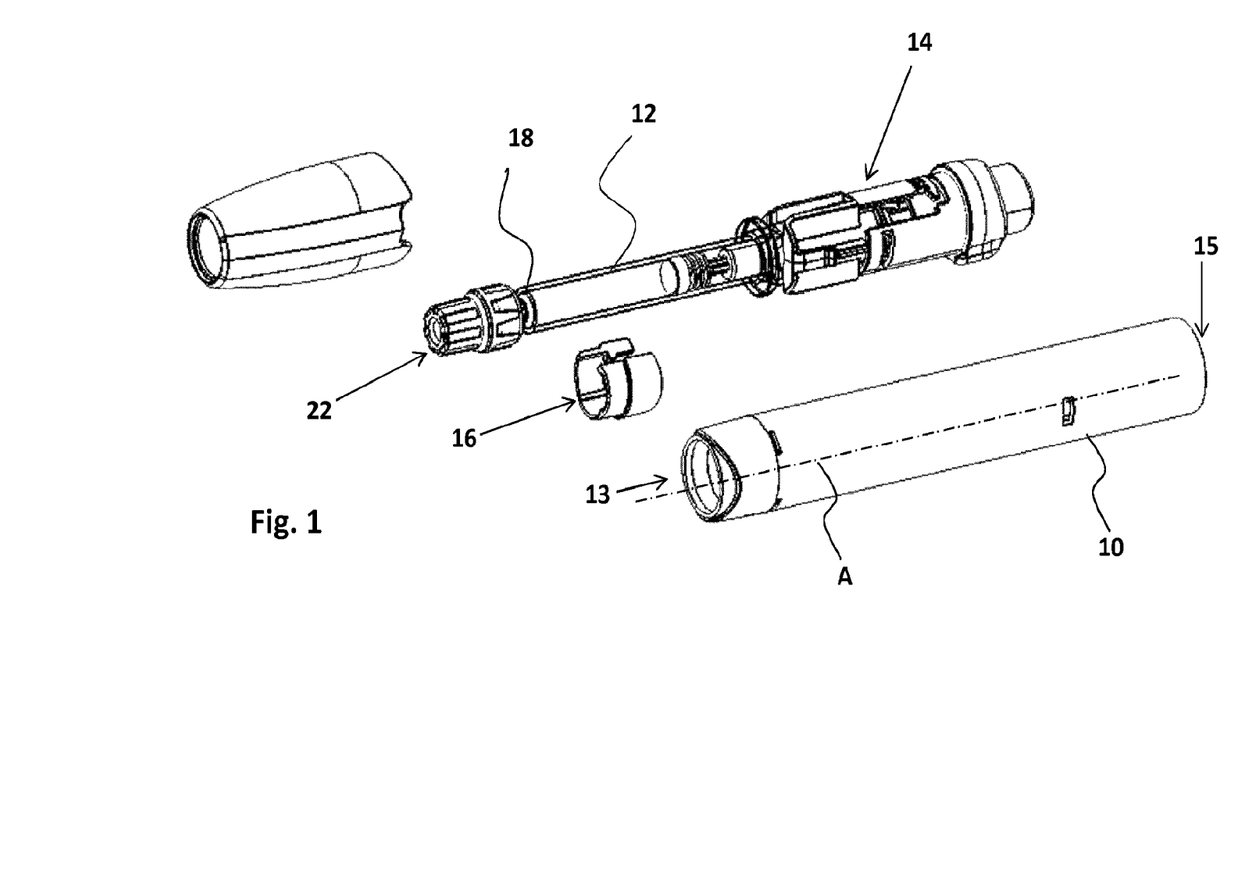
FIG. 1 is an exploded view of a medicament delivery device comprising a first embodiment of a C-shaped tubular body.

The medicament delivery device according to the present invention is intended to be utilized with a C-shaped tubular body 16 capable of holding a medicament container 12 within the medicament delivery device; preferably the medicament delivery device is an injection device and more preferably an auto-injection device FIG. 1. The medicament delivery device comprises:
- a medicament container 12 comprising a movable plunger 11, a neck portion 18 and a delivery member unit 22;
- a longitudinally extending housing 10 along a longitudinal axis A and having a proximal open end 13 and an opposing distal open end 15; and
- a drive unit 14 arranged at the distal end of the housing and configured to apply a force on the movable plunger for delivering a dose of medicament.

The medicament delivery device may further comprise auto-function means such as means for performing a penetration of an injection needle into a medicament delivery site before starting to apply a force on the movable plunger for delivering a dose of medicament and/or means for performing a retraction of the needle from the injection site after the medicament has been delivered. These features may be activated by e.g. a push button on the medicament delivery device. However, these features do not form any part of the present invention.

The medicament container 12 is preferably designed as an elongated tubular container containing the medicament and the movable plunger/resilient stopper. The medicament container has further the neck portion 18, more preferably a proximally directed neck portion, and the delivery member unit 22. The delivery member unit could either be a delivery member, preferably an injection needle, integrated with the medicament container or an attachment portion to which a delivery member, preferably an injection needle, may be attached. A preferred attachment design is a so-called luer taper system, which may include a luer lock design or a luer slip design. These designs are per se known to the person skilled in the art and will not be described in more detail. A further preferred injection needle safety system that may be used with the present invention is a tamper evident luer lock closure unit or TELC-unit.

Figure 2:
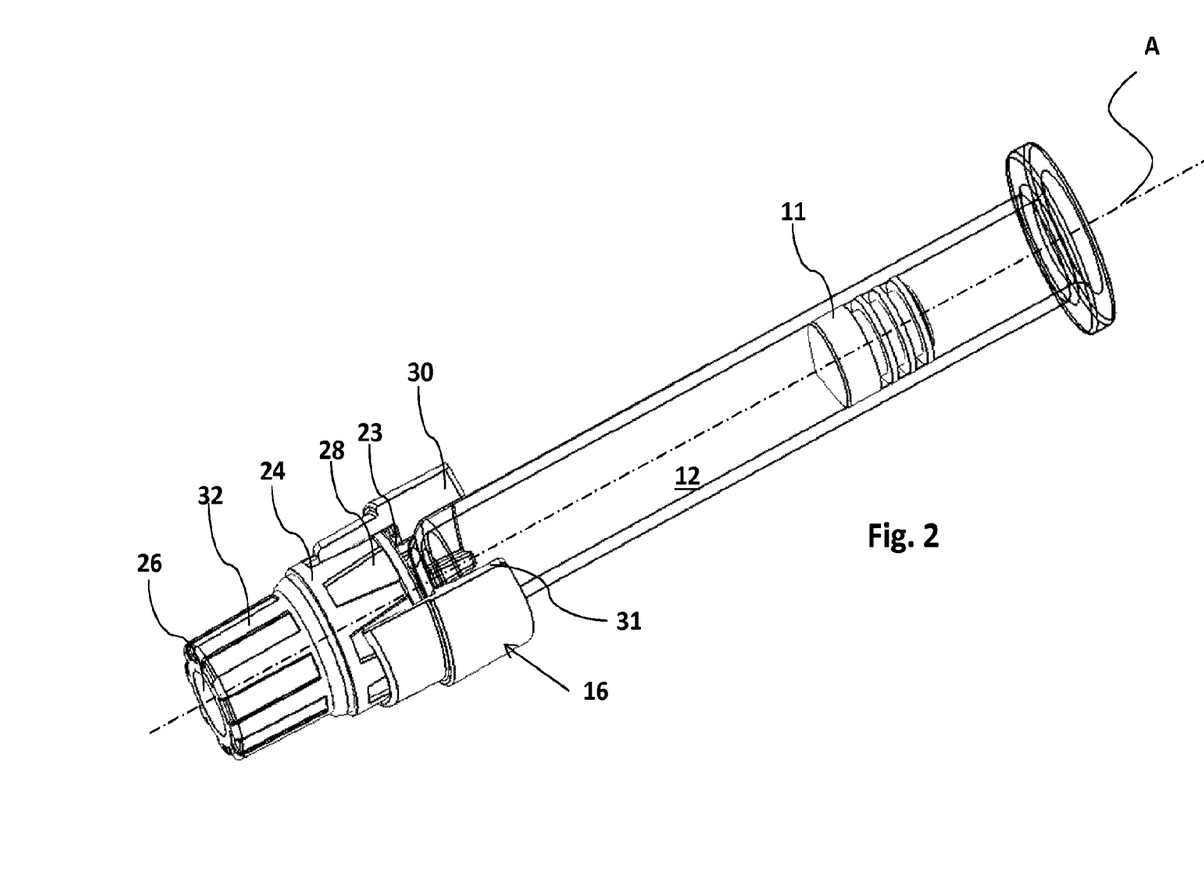
FIG. 2 is a detailed view of a medicament container provided with a TELC-unit as well as the C-shaped tubular body of FIG. 1.

The delivery member unit 22, which in the disclosed embodiment is a TELC-unit, comprises an attachment part 24 and a closure cap/shield 26, FIG. 2. The attachment part 24 is fixedly attached/connected/engaged to the proximal end of the medicament container preferably by luer-lock threads. The closure cap/shield 26 is removably connected to the attachment part, preferably threadedly engaged to the attachment part 24 such that the closure cap/shield 26 is twisted during removal from the attachment part. In order to facilitate the removal of the closure cap/shield 26, both the attachment part 24 and the closure cap/shield 26 are provided with longitudinally extending indentations 28 and ribs 32 respectively, which provide an improved grip for a user.

Figure 3:
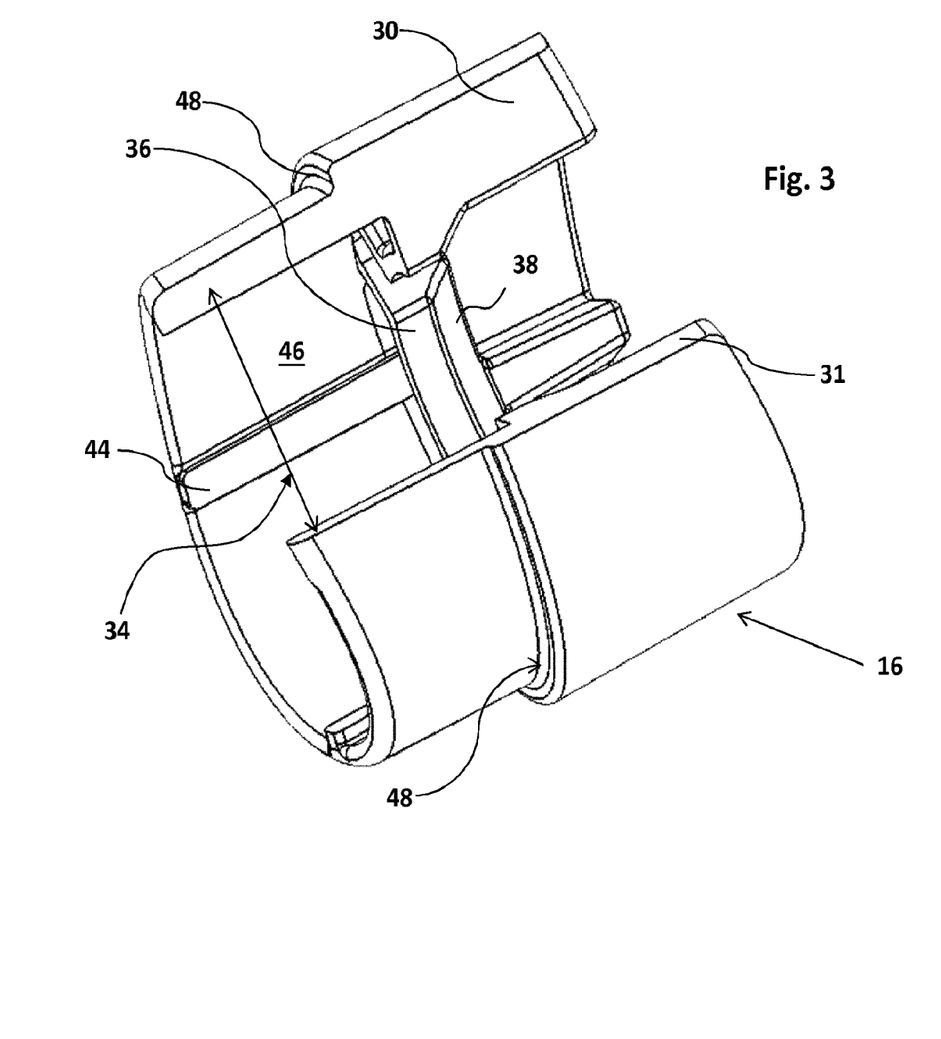
FIG. 3 is a perspective view of the C-shaped tubular body according to the first embodiment.

The C-shaped tubular body 16 is provided with a longitudinally extending slit/gap 34 of a certain width, FIG. 3. Due to the longitudinally extending slit/gap 34, the C-shaped tubular body 16 may be attached to the proximally directed neck portion 18 of said medicament container 12 forming a container unit. The C-shaped tubular body 16 is configured to interact with said TELC unit such that said medicament container is prevented to be moved in relation to the C-shaped tubular body 16 after said the C-shaped tubular body 16 is attached to the proximally directed neck portion 18 of said medicament container 12 forming the container unit. Further, the C-shaped tubular body 16 is also configured to interact with said housing 10 such that the C-shaped tubular body 16 is prevented to be moved in relation to said housing after said container unit is arranged within said housing.

Thus, the C-shaped tubular body 16 comprises inner support means configured to interact with the neck portion 18 of said medicament container 12 and with the delivery member unit 22, the TELC unit, of said medicament container 12 such that said medicament container is prevented from being moved in relation to the C-shaped tubular body, after the medicament container is attached to said C-shaped tubular body or vice versa forming the container unit, and outer support means configured to interact with corresponding support means of the housing 10 such that said C-shaped tubular body is prevented from being moved in relation to the housing after the container unit is arranged within said housing through the distal open end.

Figure 4:
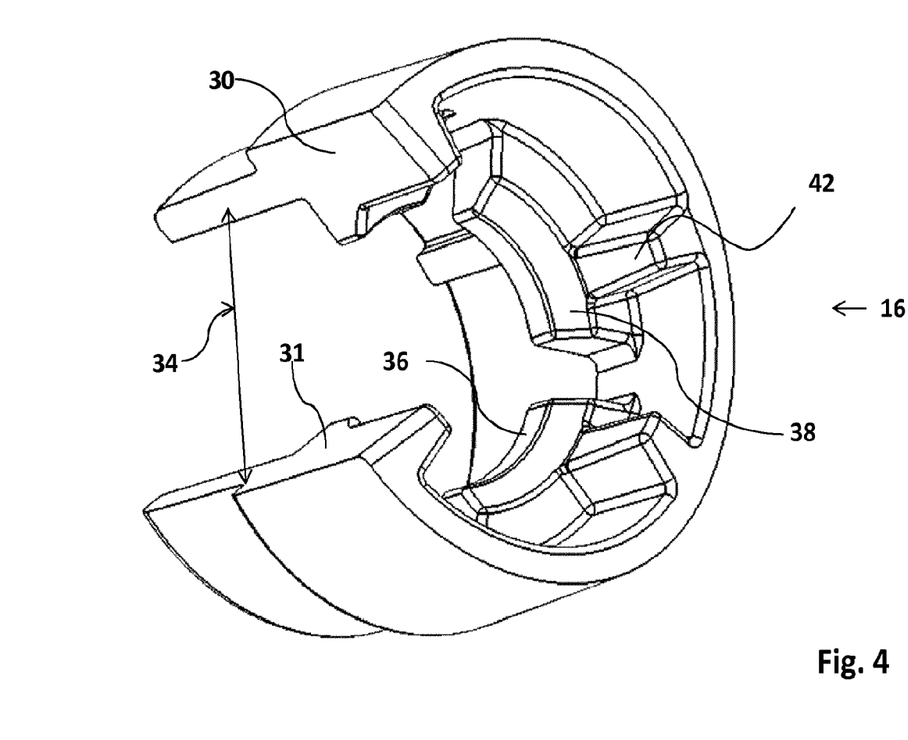
FIG. 4 is a perspective view of the C-shaped tubular body of FIG. 3.

The inner support means, FIG. 3, comprises at least one longitudinally extending and radial inwardly directed ledge 44 on the inner circumferential surface of the C-shaped tubular body. Said longitudinally extending and radial inwardly directed ledge 44 is configured to interact with at least one longitudinally extending indentation 28 on the outer surface of the attachment part, such that said medicament container is prevented from being rotated in relation to the C-shaped tubular body. The inner support means further comprises a continuous annular radial inwardly directed ledge 36 or discrete annular radial inwardly directed ledges on the inner circumferential surface of the C-shaped tubular body configured to interact with the neck portion of said medicament container 12 and with the distal annular surface 23 of the attachment part 24, such that said medicament container is prevented from being longitudinally moved in relation to the C-shaped tubular body. As shown in FIG. 4, the distally directed part of the continuous annular radial inwardly directed ledge 36 or the distally directed part of each of the discrete annular radial inwardly directed ledges is preferably arranged with a bevelled surface 38 having an inclination that generally corresponds to the inclination of the neck portion 18 of the medicament container 12. The inner circumferential surface of the tubular body 16 on the distal side of the first support means 36 may further be provided with support members 42 for preventing the movement of the medicament container in radial directions, FIG. 4. Preferably, said support members 42 are longitudinally extending and radial inwardly directed ledges/ribs that support the medicament container.

Figure 6:
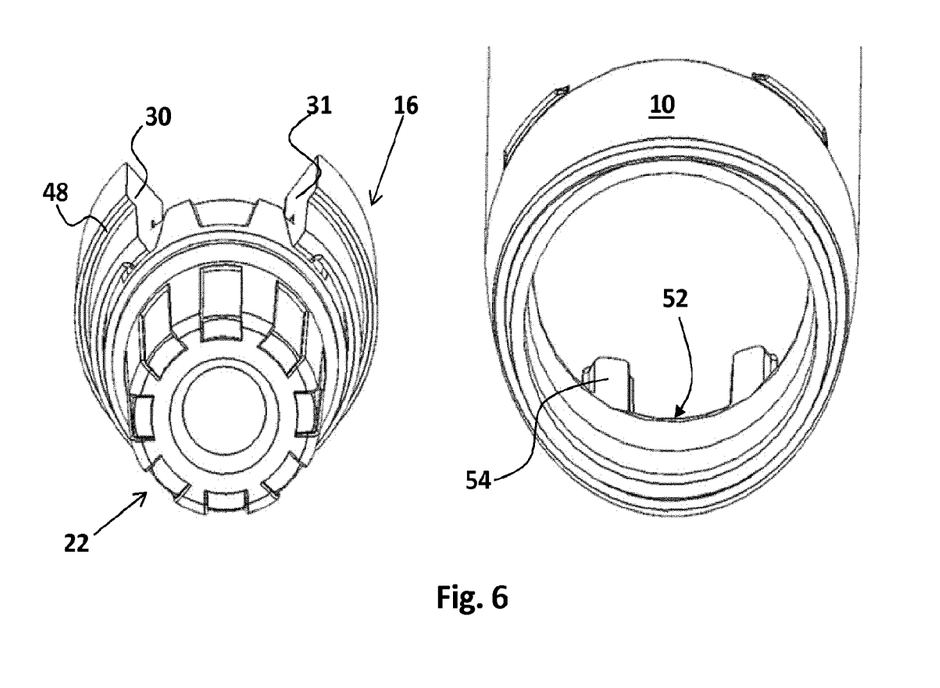
FIG. 6 is a perspective detailed view of a proximal part of a housing section of the medicament delivery device.

In the shown embodiment in FIGS. 2 and 6, the delivery member unit 22 is preferably a TELC-unit and the inner circumferential surface of the tubular body 16 is divided by the continuous annular radial inwardly directed ledge 36 or discrete annular radial inwardly directed ledges in two parts, a proximal and a distal inner surface. The proximal inner surface being configured to house the attachment part 24 of the TELC-unit and the distal inner surface being configure to house a part of the container. Preferably, the inner diameter of the proximal inner surface is set to generally correspond to the outer diameter of the attachment part 24 of the TELC-unit so that the attachment part 24 is housed in the proximal inner surface. More preferably, said at least one longitudinally extending and radial inwardly directed ledge 44 is arranged on the proximal inner surface for rotationally holding said attachment part 24 and thereby preventing said medicament container to be rotated in relation to the tubular body 16.

The outer support means, FIG. 6, comprises a continuous annular surface 48 or discrete annular surfaces on the outer circumferential surface of the C-shaped tubular body facing towards the proximal end of the device configured to interact with a corresponding continuous annular surface or discrete annular surfaces 52 arranged on the inner circumferential surface of the housing facing towards the distal end of the device, such that said C-shaped tubular body is prevented from passing through the proximal open end of the housing after the container unit is arranged within said housing through the distal open end of the housing. The outer support means, FIG. 3, further comprises first and second opposed lateral edges 30, 31 forming the longitudinally extending slit/gap 34, said lateral edges being configured to interact with longitudinally extending and radial inwardly directed ledges or ribs 54 arranged on the inner circumferential surface of the housing, FIG. 6, such that the container unit is prevented to be rotated in relation to the housing.

Figure 5:
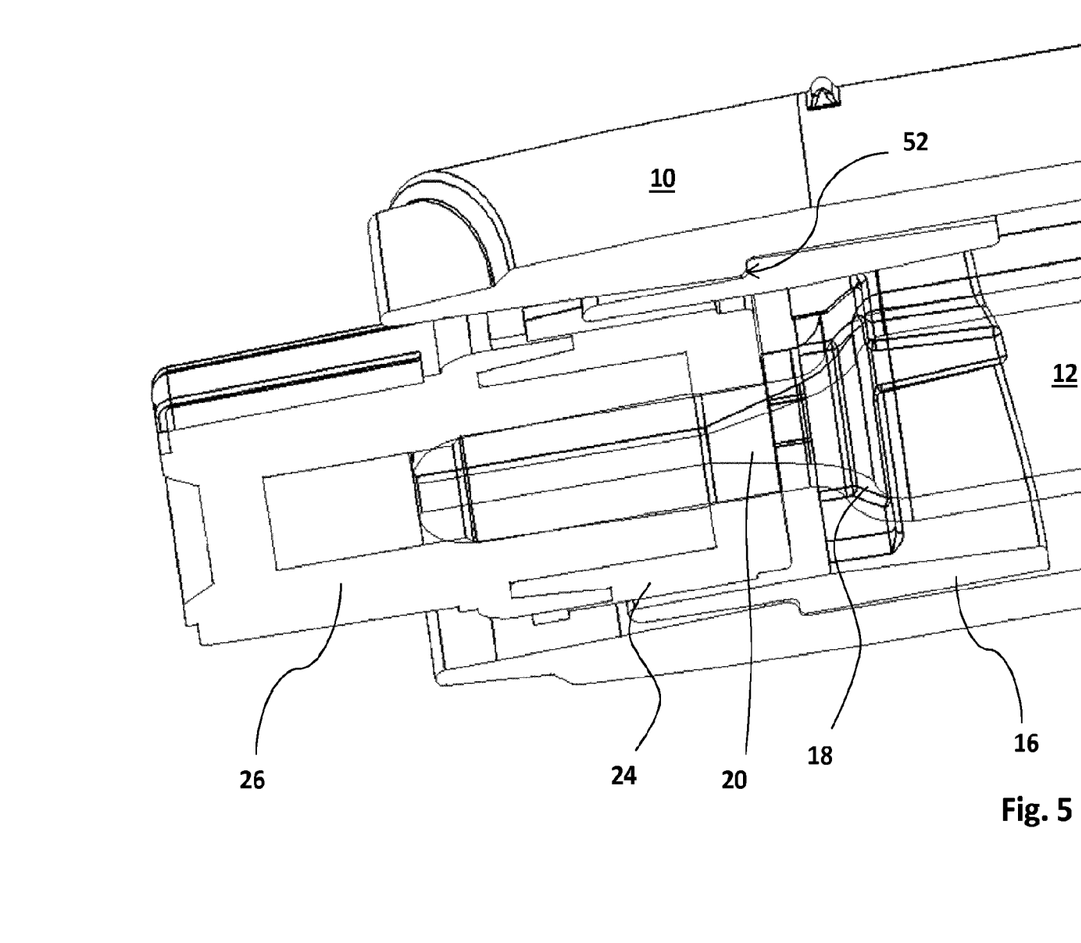
FIG. 5 is a cross-sectional view of a proximal part of a medicament delivery device comprising the C-shaped tubular body of FIG. 3.

In a first embodiment as shown in FIG. 5, when the tubular body 16 together with the medicament container 12 are arranged within said housing, the continuous annular surface 52 on the inner circumferential surface of the housing abut(s) the corresponding continuous annular surface 48 on the outer circumferential surface of the tubular body 16, such that the tubular body 16 is prevented from being moved/displaced in a longitudinal direction towards the proximal end in relation to the housing. In a variant of the first embodiment (not shown), when the tubular body 16 together with the medicament container 12 are arranged within said housing, the discrete annular surfaces on the inner circumferential surface of the housing are engaged to the corresponding discrete annular surfaces on the outer circumferential surface of the tubular body 16, such that the tubular body 16 is prevented from being moved/displaced in a longitudinal direction towards the proximal end in relation to the housing and also prevented from being rotated in relation to the housing.

When the first embodiment of the present invention is to be used, the slit/gap 34 of the tubular body 16 is pushed against the body of the medicament container 12. This causes tubular body 16 to flex such that the body of the medicament container 12 fits into the tubular body 16. The tubular body 16 is then moved/pushed in the proximal direction until the continuous annular radial inwardly directed ledge or the discrete annular radial inwardly directed ledges 36, reach(es) the neck portion 18 of the medicament container 12 whereby the bevelled surface(s) 38 are/is in contact with the neck portion 18 of the medicament container. Further, the proximal inner surface 46 of the tubular body 16 surrounds the outer circumferential surface of the attachment part 24 of the TELC-unit 22 such that the longitudinally extending and radial inwardly directed ledges 44, abut/engage with the corresponding longitudinally extending and radial outwardly directed ledges 28 on the attachment part 24 of the TELC-unit 22, whereby the attachment part 24 together with the medicament container 12 are prevented from being rotated in relation to the tubular body 16.

The medicament container 12 with the TELC-unit 22 is now attached to the tubular body 16 or vice versa forming a container unit. Said container unit can now be inserted into/within the housing 10 of the medicament delivery device from a distal direction. During insertion, the container unit is guided such that the slit/gap 34 of the tubular body 16 is engageable or engages with the longitudinally extending and radial inwardly directed ledges or ribs 54, on the inner circumferential surface of the housing whereby the container unit is prevented to be rotated in relation to the housing. Further, the continuous annular surface on the outer circumferential surface 48 of the tubular body 16 abut with the corresponding continuous annular surface 52 on the inner circumferential surface of the housing 10 whereby the container unit is prevented from being moved in a longitudinal direction towards the proximal end in relation to the housing. In this position, the closure cap/shield 26 protrudes through a proximally directed opening of the housing 10 so that a user may grip the closure cap/shield 26 for removal.

Then, a power pack, a distal housing part or whatever the medicament delivery device may be provided with regarding activation features, may be connected to the distal area of the housing, thereby also locking the medicament container in the distal direction.

FIGS. 7 to 10 display a second embodiment of the invention. It comprises a holder for a medicament container where the holder has a generally C-shaped tubular body 160. In many ways, the C-shaped body 160 of the second embodiment displays the same features as the C-shaped body 16 of the first embodiment. The C-shaped tubular body 160 of the second embodiment is however longer in the longitudinal direction, surrounding at least parts of the medicament container in the distal direction. The C-shaped tubular body is arranged with a longitudinally extending slit/gap 134, providing a means for attaching the C-shaped tubular body to a medicament container 12 in the same manner as described above. However, since the C-shaped tubular body of the second embodiment is longer, a larger part in the longitudinal direction, of the medicament container will be covered by the C-shaped tubular body. The C-shaped tubular body is further arranged with a longitudinally extending cut-out or slit 142, where the slit/gap 134 and the slit 142 form flexing members, the function of which will be explained below.

The C-shaped tubular body 160 comprises inner support means configured to interact with the neck portion 18 of said medicament container 12 and with the delivery member unit 22, the TELC unit, of said medicament container 12 such that said medicament container is prevented from being moved in relation to the C-shaped tubular body, after the medicament container is attached to said C-shaped tubular body or vice versa forming the container unit. The C-shaped tubular body 160 further comprises outer support means configured to interact with corresponding support means of the housing 100 such that said C-shaped tubular body is prevented from being moved in relation to the housing after the container unit is arranged within said housing through the distal open end.

Figure 8:
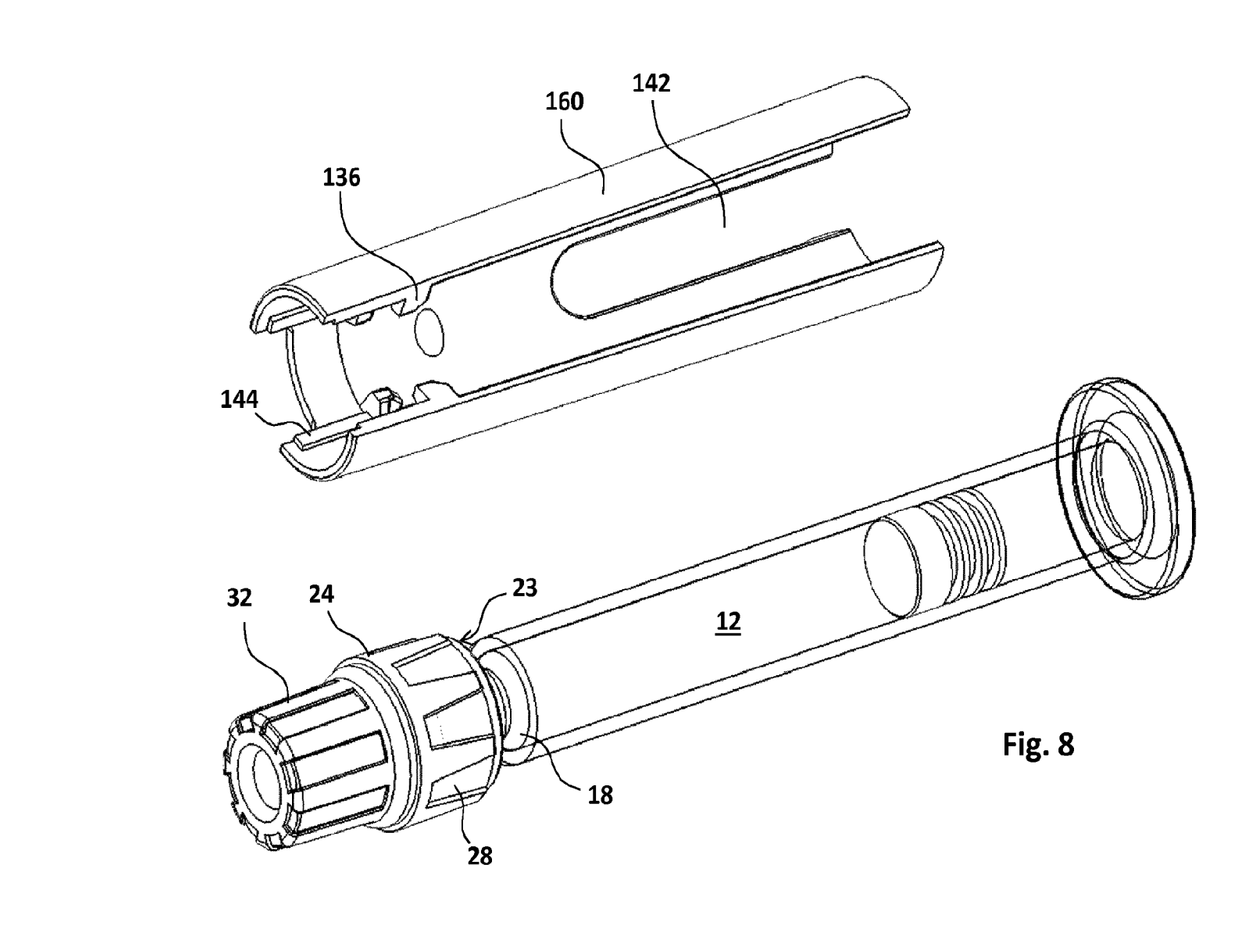
FIG. 8 is a detailed view of a medicament container provided with a TELC-unit as well as the C-shaped tubular body of FIG. 7.
Figure 9:
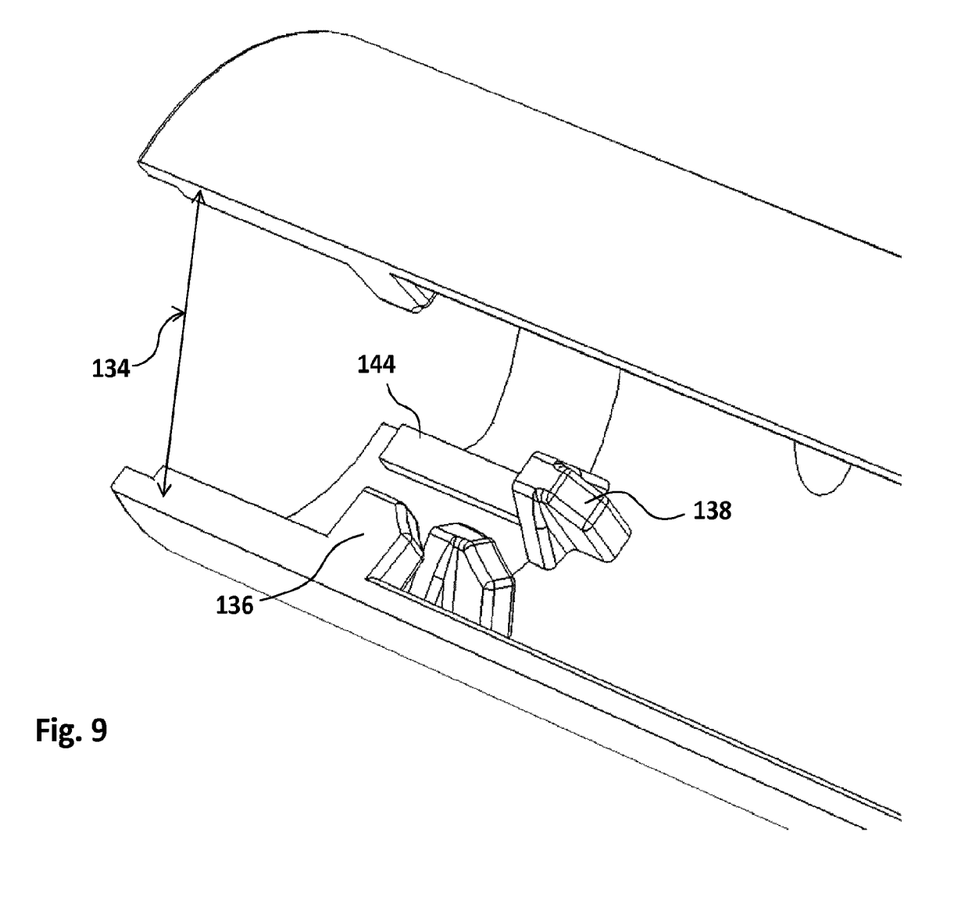
FIG. 9 is a perspective view of the C-shaped tubular body according to the second embodiment.
Figure 10:
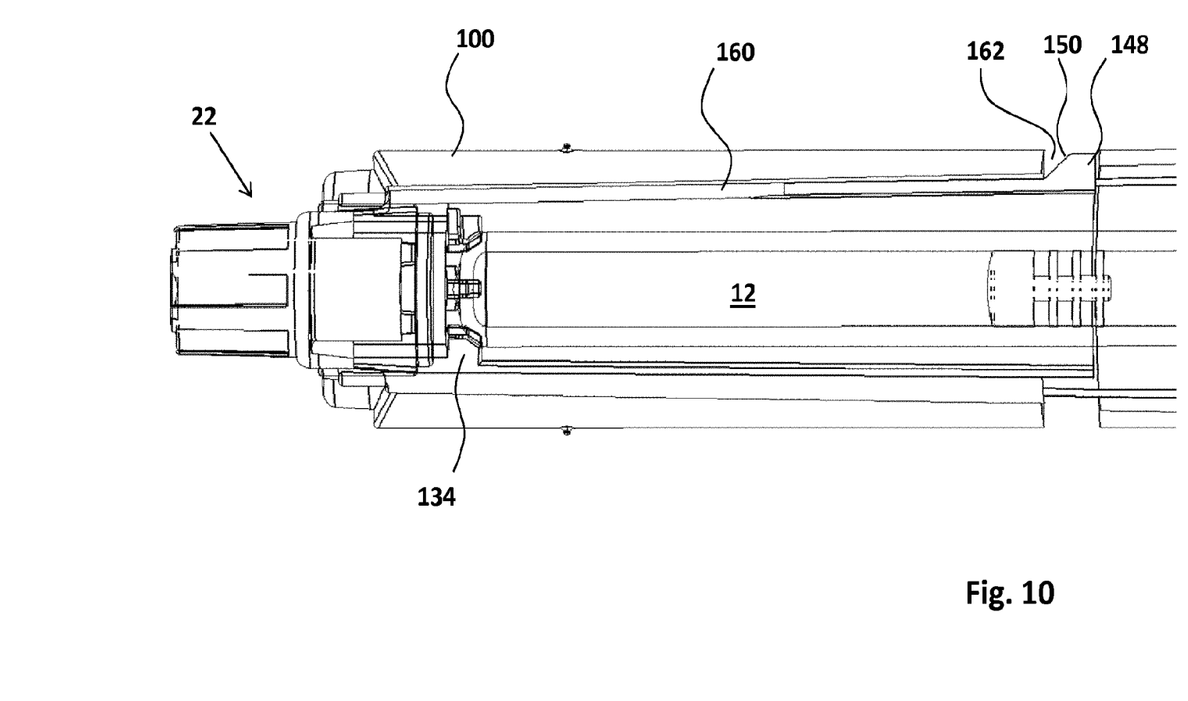
FIG. 10 is a cross-sectional view of a proximal part of a medicament delivery device according to the second embodiment.

The inner support means, FIGS. 8 and 9, comprises at least one longitudinally extending and radial inwardly directed ledge 144 on the inner circumferential surface of the C-shaped tubular body 160. Said longitudinally extending and radial inwardly directed ledge 144 is configured to interact with at least one longitudinally extending indentation 28, FIG. 8, on the outer surface of the attachment part 24, such that said medicament container is prevented from being rotated in relation to the C-shaped tubular body. The inner support means further comprises discrete annular radial inwardly directed ledges 136 or a continuous annular radial inwardly directed ledge on the inner circumferential surface of the C-shaped tubular body 160 configured to interact with the neck portion 18 of said medicament container 12 and with the distal annular surface 23 of the attachment part 24, such that said medicament container 12 is prevented from being longitudinally moved in relation to the C-shaped tubular body. As shown in FIG. 9, the distally directed part of each of the discrete annular radial inwardly directed ledges 136 is preferably arranged with bevelled surfaces 138 having an inclination that generally corresponds to the inclination of the neck portion 18 of the medicament container 12. The bevelled surfaces 138 are arranged for preventing the movement of the medicament container 12 in a proximal axial direction as well as in radial directions.

Figure 7:
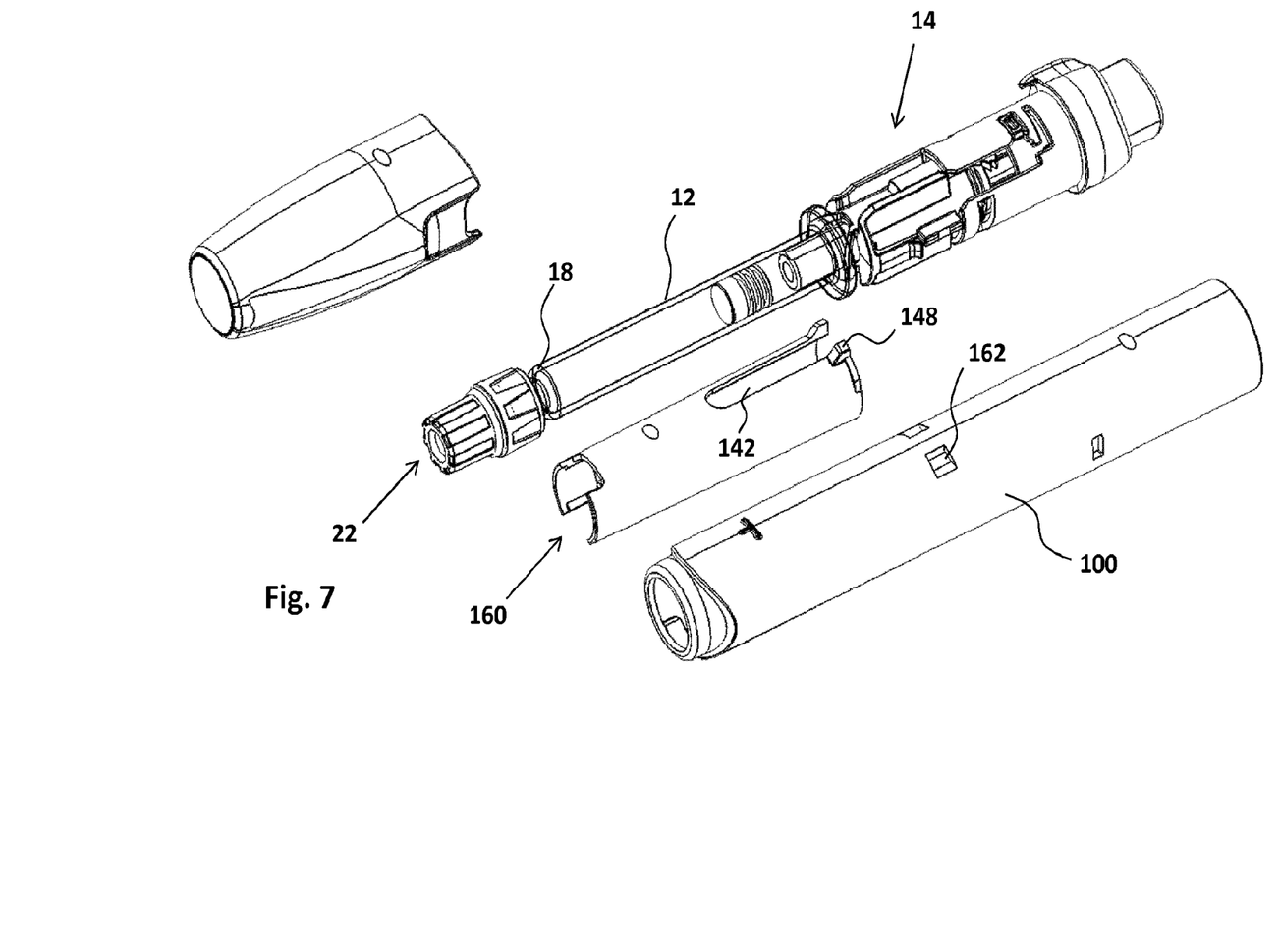
FIG. 7 is an exploded view of a medicament delivery device comprising a second embodiment of a C-shaped tubular body.

The outer support means, FIG. 7, comprises a number of outwardly directed protrusions 148. In the embodiment shown in FIG. 7, the protrusions are arranged at a distal end of the C-shaped tubular body 160. However, it is to be understood that the protrusions may be positioned on other locations on the outer surface of the C-shaped tubular body 160. The protrusions are arranged to fit into seats 162 in the form of recesses or cut-outs in the housing 100, FIG. 10, providing a lock between the C-shaped tubular body 160 and the housing 100, effectively preventing movement of the C-shaped tubular body 160 both in the longitudinal direction as well as in the rotational direction. The protrusions 148 are arranged with a proximally directed inclined surface 150 that together with the slit/gap 134 and the cut-out 142 of the C-shaped body facilitates insertion and attachment to the housing 10.

It is to be understood that the embodiment described above and shown in the drawings is to be regarded only as a non-limiting example of the invention and that it may be modified in many ways within the scope of the patent claims.

The invention claimed is:

1. A C-shaped tubular body comprising a longitudinally extending gap such that the C-shaped tubular body can be attached to a neck portion of a medicament container, said C-shaped tubular body comprising:
   an inner support configured to interact with the neck portion and with a delivery unit of the medicament container such that the medicament container is prevented from being moved in relation to the C-shaped tubular body after the medicament container is attached to the C-shaped tubular body, and
   an outer support configured to interact with a corresponding support of a medicament container housing such that the C-shaped tubular body is prevented from being moved in relation to the medicament container housing after the container unit is arranged within the medicament container housing.

2. The C-shaped tubular body of claim 1, wherein said delivery unit comprises an attachment part.

3. The C-shaped tubular body of claim 2, wherein the inner support comprises at least one longitudinally extending directed ledge on an inner surface of the C-shaped tubular body configured to interact with at least one longitudinally extending indentation on an outer surface of the attachment part, such that said medicament container is prevented from being rotated in relation to the C-shaped tubular body.

4. The C-shaped tubular body of claim 3, wherein the inner support further comprises a ledge provided along the inner circumferential surface of the C-shaped tubular body and configured to interact with the neck portion of the medicament container.

5. The C-shaped tubular body of claim 4, wherein the ledge provided along the inner circumferential surface of the C-shaped tubular body comprises a continuous ledge.

6. The C-shaped tubular body of claim 4 wherein the ledge of the inner support is configured to interact with an annular surface of the attachment part, such that the medicament container is prevented from being moved in relation to the C-shaped tubular body.

7. The C-shaped tubular body of claim 1, wherein the outer support comprises at least one annular surface on the outer surface of the C-shaped tubular body facing towards the proximal end of the device and is configured to interact with a corresponding annular surface arranged on the inner surface of the medicament container housing facing towards the distal end of the device, such that said C-shaped tubular body is prevented from passing through a proximal open end of the medicament container housing after the container unit is arranged within the medicament container housing.

8. The C-shaped tubular body of claim 7, wherein the outer support further comprises a first lateral edge and a second lateral edge forming the longitudinally extending gap.

9. The C-shaped tubular body of claim 8 wherein, the first lateral edge and the second lateral edge are configured to interact with longitudinally extending directed ledge arranged on the inner surface of the medicament container housing, such that the container unit is prevented from being rotated in relation to the medicament container housing.

10. The C-shaped tubular body of claim 1, wherein the outer support comprises at least one outwardly extending protrusion on an outer surface of said C-shaped tubular body, the at least one outwardly extending protrusion configured to interact with at least one seat provided on an inner surface of the medicament container housing.

11. The C-shaped tubular body of claim 10, further comprising:

at least one flexing member for facilitating an interaction between the at least one outwardly extending protrusion and the at least one seat.

12. The C-shaped tubular body of claim 11, wherein the at least one protrusion is arranged with an inclined surface for facilitating the interaction between the at least one protrusion and the at least one seat.

13. The C-shaped tubular body of claim 11, wherein the at least one protrusion is arranged at a distal end of the C-shaped tubular body.

14. The C-shaped tubular body of claim 1 wherein the delivery unit comprises a TELC-unit.

15. A method of assembling a C-shaped body to a medicament container, the method comprising the steps of:
pushing a C-shaped body against a body of a medicament container;
flexing the C-shaped body;
fitting the medicament container into the C-shaped body;
pushing the C-shaped body in a proximal direction until an annual radial inwardly directed ledge of C-shaped body reaches a neck portion of the medicament container; and
contacting the neck portion of the medicament container with at least one beveled surface of the C-shaped body.

16. The method of claim 15 further comprising the step of surrounding an outer circumferential surface of an attachment part by a proximal inner surface of the C-shaped body.

17. The method of claim 16 further comprising the step of engaging longitudinally extending directed ledges of the C-shaped body with corresponding longitudinally extending directed ledges on the attachment part.

18. The method of claim 17 further comprising the step of preventing the attachment part from rotating in relation to the C-shaped body.

19. The method of claim 18 further comprising the step of preventing the medicament container from rotating in relation to the C-shaped body.

20. The method of claim 17 further comprising the step of forming a container unit by attaching the attachment part with the medicament container to the C-shaped body.

21. The method of claim 20 further comprising the step of inserting the container unit into a medicament delivery device housing.

22. The method of claim 21 further comprising the step of distally inserting the container unit into the medicament delivery device housing.

23. The method of claim 21 further comprising the step of: guiding the container unit while the container unit is inserted into the medicament delivery device housing.

24. The method of claim 23 further comprising the step of: engaging a gap of the C-shaped body with at least one longitudinal ledge on an inner surface of the medicament delivery device housing.

25. The method of claim 24 further comprising the step of: preventing the container unit from rotating in relation to the medicament delivery device housing.

26. The method of claim 25 further comprising the step of: abutting an annular surface on the outer surface of the tubular body with a corresponding annular surface on the inner surface of the medicament delivery device housing.

27. The method of claim 26 further comprising the step of: preventing the container unit from being moved in a longitudinal direction in relation to the medicament delivery device housing.

28. The method of claim 27 further comprising the step of: connecting a distal housing part to a distal area of the medicament delivery device housing.

29. The method of claim 28 further comprising the step of: locking the medicament container in a distal direction.

* * * * *